(12) United States Patent
Stauffer

(10) Patent No.: US 7,683,230 B2
(45) Date of Patent: Mar. 23, 2010

(54) METHYL BROMIDE TO OLEFINS

(76) Inventor: John E. Stauffer, 6 Pecksland Rd., Greenwich, CT (US) 06830

(*) Notice: Subject to any disclaimer, the term of this patent is extended or adjusted under 35 U.S.C. 154(b) by 287 days.

(21) Appl. No.: 11/260,757

(22) Filed: Oct. 27, 2005

(65) Prior Publication Data

US 2007/0100189 A1 May 3, 2007

(51) Int. Cl.
*C07C 1/00* (2006.01)
(52) U.S. Cl. ...................... 585/641; 585/638
(58) Field of Classification Search ................ 585/638, 585/641
See application file for complete search history.

(56) References Cited

U.S. PATENT DOCUMENTS

| | | | |
|---|---|---|---|
| 2,320,274 A * | 5/1943 | Gorin | 585/322 |
| 2,488,083 A * | 11/1949 | Gorin et. al. | 585/642 |
| 3,697,611 A * | 10/1972 | Magoon | 585/637 |
| 6,452,058 B1 * | 9/2002 | Schweizer et al. | 570/223 |
| 2005/0027084 A1 * | 2/2005 | Clarke et al. | 526/68 |

* cited by examiner

*Primary Examiner*—In Suk Bullock
(74) *Attorney, Agent, or Firm*—Young Basile

(57) ABSTRACT

The specification discloses a process for the production of olefins including ethylene, propylene and butenes from methyl bromide. In a chemical reaction methyl bromide is dehydrobrominated to the olefin and hydrogen bromide. The reaction is carried out at elevated temperatures, preferably in the range of 300° C. to 500° C. A catalyst comprising a zeolite may be used.

4 Claims, 1 Drawing Sheet

METHYL BROMIDE TO OLEFINS

FIELD OF THE INVENTION

The present invention relates to a process for producing olefins, including ethylene, propylene and butenes, from methyl bromide. In the process, methyl bromide undergoes a chemical reaction to produce the olefin and hydrogen bromide. By recycling the hydrogen bromide, a stand-alone process is feasible.

BACKGROUND OF THE INVENTION

New technology has been reported for the synthesis of olefins from methanol. (*Chemical Engineering*, January 1996, page 17). As described in the literature, this process converts methanol in a fluidized-bed reactor at a pressure between 1 and 5 atmospheres and a temperature in the range of 350° C. to 500° C. A zeolite-type of catalyst consisting of silicon-aluminum-phosphorous oxide is used to promote the reaction.

The process is capable of converting at best about 80 percent of the methanol to ethylene and propylene in varying proportions of these olefins. The reaction is exothermic and therefore the heat of reaction must be removed by suitable means. Although this process promises to free manufacturers from reliance on traditional feedstocks, e.g., naphtha, it nevertheless is tied to the economics of methanol.

Notwithstanding interest expressed in this new technology for producing olefins from methanol, there is some concern about its limitations. Therefore it is an object of the present invention to offer an improved method for the manufacture of olefins. This object as well as other features and advantages will be apparent from the following description and the FIGURE which is included.

SUMMARY OF THE DISCLOSURE

The specification discloses a process for the synthesis of olefins including ethylene, propylene and butenes from methyl bromide. A novel chemical reaction is employed whereby two or more methyl bromide molecules combine with each other to form the desired olefin plus byproduct hydrogen bromide. This reaction will occur when the methyl bromide is heated to a sufficiently high temperature.

A catalyst, however, may be employed in the reaction in order to provide improved yields of product or to give greater selectivity of the desired olefin. Such a catalyst may comprise the salts of copper, zinc and bismuth; alumina gel; silica-alumina molecular sieves; and silicon-aluminum-phosphorous oxide zeolites.

Although the reaction may be carried out in a wide range of temperatures, the preferred operating condition is between about 300° C. and about 500° C. Likewise, a wide range of pressures can be used. From a practical standpoint, the favored pressure is in the range of about 1 bar to approximately 5 bars.

For maximum efficiency, a continuous reactor is employed in the process. In order to maintain the operating temperature, an external source of heat is needed. The effluent from the reactor is cooled before recovering the desired olefins.

DETAILED DESCRIPTION OF THE PROCESS

Figure 1:
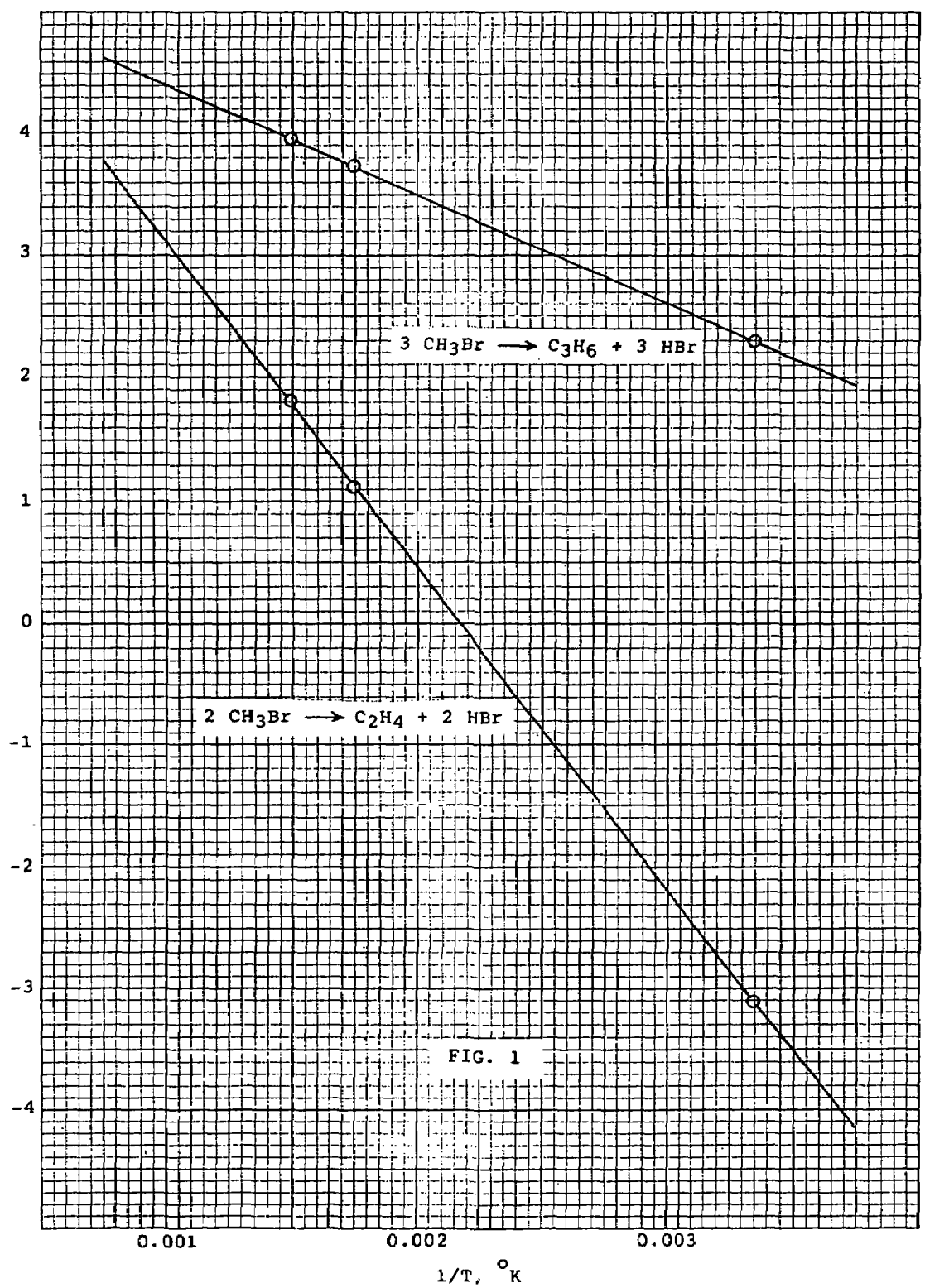
FIG. 1 is a graph showing the equilibrium conversions of methyl bromide to ethylene and propylene at given temperatures.

The process of the present invention comprises a chemical reaction whereby methyl bromide ($CH_3Br$) is condensed to form an olefin plus hydrogen bromide (HBr). The olefin may include ethylene ($C_2H_4$), propylene ($C_3H_6$), and butene ($C_4H_8$). In addition some higher olefins will inevitably be formed. By adjusting the reaction conditions and employing a specific catalyst, the ratios of these various olefins may be modified. Thus, the process can yield a mixture containing 50 percent ethylene and 30 percent propylene or a mixture with 40 percent ethylene and 40 percent propylene.

The reactions for the formation of ethylene and propylene can be illustrated by the following equations.

$$2CH_3Br \rightarrow C_2H_4 + 2HBr \qquad 1.$$

$$3CH_3Br \rightarrow C_3H_6 + 3HBr \qquad 2.$$

These reactions are carried out in the gas phase and may be promoted by a heterogeneous catalyst.

The conversions of methyl bromide to various olefins under equilibrium conditions can be determined by thermodynamic calculations. Thus, log Kp, where Kp is the equilibrium constant, equals 1.13 at 300° C. for the conversion of methyl bromide to ethylene. At 400° C. log $K_p$ is 1.81 for the same reaction.

Likewise, for the conversion of methyl bromide to propylene, log $K_p$ is 3.73 at 300° C., and 3.96 at 400° C. These results are shown graphically in FIG. 1. From these curves, it is apparent that favorable conversions, where log $K_p$ equals zero or greater, can be attained at temperatures above 188° C.

Thermodynamic calculations also indicate that both reactions are endothermic, i.e., they absorb heat. Thus, in order to control the reaction temperature, heat must be supplied from an external source such as a furnace.

Although the reactions will occur at sufficiently high temperatures without a catalyst, there are advantages in using one. First, less severe conditions, e.g., lower temperatures, can be used. Second, improved yields are possible and third, some control over product selectivity can be realized.

Effective catalysts can be determined from the reaction mechanism. A plausible mechanism is postulated from known chemical reactions. It is established that methyl bromide can be prepared from methanol ($CH_3OH$) and hydrogen bromide. This reaction is reversible whereby methyl bromide is hyrdrolyzed with water ($H_2O$). Furthermore, the prior art discloses the formation of olefins from methanol. These two reactions can be represented by equations for the synthesis of ethylene as follows.

$$2CH_3Br + 2H_2O \leftrightarrow 2CH_3OH + 2HBr \qquad 3.$$

$$2CH_3OH \rightarrow C_2H_4 + 2H_2O \qquad 4.$$

When equations 3 and 4 are combined, the result is the same as equation 1. It should be noted that the water required for equation 3 is supplied by the water produced in equation 4. Quite likely, there is enough moisture present in the feed gas to initiate these reactions. Otherwise some water may be chemisorbed on the catalyst.

Both equations 3 and 4 represent catalytic reactions. The hydrolysis reaction of equation 3 is catalyzed by salts of copper, zinc and bismuth as well as by alumina gel and silica-alumina catalysts. The dehydration reaction of equation 4 is catalyzed by silica-alumina based molecular sieves and by silicon-aluminum-phosphorous oxide zeolites.

In view of these findings a preferred catalyst would be a silica-alumina catalyst modified with other elements. Such a catalyst would be active in the range of about 300° C. to about 500° C. An applied pressure of 1 to 5 bars would be suitable.

The process of the present invention unavoidably generates byproduct hydrogen bromide. In order for the process to be economical, some way must be found to recycle this material. One solution would be to react hydrogen bromide with synthesis gas containing hydrogen and carbon monoxide to produce additional methyl bromide. In this manner, the process could be made self-supporting.

What is claimed is:

1. A process for the manufacture of an olefin from methanol comprising:

(a) reacting hydrogen bromide with methanol a catalytic reaction to form methyl bromide and water,
   (b) condensing the methyl bromide by pyrolysis at a temperature in the range of 300° C. to 500° C. to form a product consisting essentially of the olefin and hydrogen bromide; and
   (c) recycling the hydrogen bromide produced in step (b) to step (a).

2. The process of claim 1, wherein the olefin is ethylene.
3. The process of claim 1, wherein the olefin is propylene.
4. The process of claim 1, wherein the olefin is butene.

* * * * *